United States Patent
Menzel et al.

(10) Patent No.: US 9,631,055 B2
(45) Date of Patent: Apr. 25, 2017

(54) PROCESS FOR THE PREPARATION OF A POLYSULFIDE

(71) Applicant: Akzo Nobel Chemicals International B.V., Amersfoort (NL)

(72) Inventors: Manfred Menzel, Greiz (DE); Daniela Lungu, Gera (DE); Olaf Klobes, Greiz (DE); Heinz Aldenhoven, Monchengladbach (DE); Antonius Van Pelt, Didam (NL); Volker Burkhardt, Morfelden-Waldorf (DE)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 14/897,425

(22) PCT Filed: Jun. 13, 2014

(86) PCT No.: PCT/EP2014/062306
§ 371 (c)(1),
(2) Date: Dec. 10, 2015

(87) PCT Pub. No.: WO2014/202467
PCT Pub. Date: Dec. 24, 2014

(65) Prior Publication Data
US 2016/0145394 A1    May 26, 2016

(30) Foreign Application Priority Data
Jun. 17, 2013 (EP) .................................... 13172268

(51) Int. Cl.
| | | |
|---|---|---|
| *C08G 75/14* | (2006.01) | |
| *C08G 75/16* | (2006.01) | |
| *C08G 75/00* | (2006.01) | |
| *C07C 41/56* | (2006.01) | |
| *C07C 43/315* | (2006.01) | |

(52) U.S. Cl.
CPC .............. *C08G 75/16* (2013.01); *C07C 41/56* (2013.01); *C07C 43/315* (2013.01); *C08G 75/00* (2013.01); *C08G 75/14* (2013.01)

(58) Field of Classification Search
CPC ....... C08L 81/04; C08G 75/025; C08G 75/14; C08G 75/16
See application file for complete search history.

(56) References Cited

U.S. PATENT DOCUMENTS

| | | | |
|---|---|---|---|
| 2,382,874 A * | 8/1945 | Gresham et al. | C08G 4/00 568/600 |
| 2,553,206 A | 5/1951 | Patrick | |
| 2,728,748 A | 12/1955 | Davis | |
| 3,305,536 A | 2/1967 | Warner | |
| 3,647,766 A | 3/1972 | Bertozzi | |
| 4,124,645 A | 11/1978 | Bertozzi | |
| 2003/0050511 A1 | 3/2003 | Gilmore et al. | |
| 2006/0094831 A1 | 5/2006 | Choi et al. | |
| 2007/0249860 A1 | 10/2007 | Zeitler et al. | |

FOREIGN PATENT DOCUMENTS

| | | |
|---|---|---|
| DE | 35849 | 1/1965 |
| DE | 238967 A1 | 9/1986 |
| DE | 251257 A3 | 11/1987 |
| EP | 0043043 A1 | 1/1982 |
| WO | 2006/037442 A1 | 4/2006 |
| WO | 2007/101819 A1 | 9/2007 |

OTHER PUBLICATIONS

European Search Report for EP13172268.8, dated Sep. 18, 2013.
International Search Report and Written Opinion for PCT/EP2014/062306, date of mailing Jul. 15, 2014.
Kirk-Othmer,Encyclopedia of Chemical Technology, 3$^{rd}$ Ed., vol. 18, Plant-Growth Substances to Potassium Compounds, Polymers Containing Sulfur (Polysulfides), p. 815.
J.R. Panek, XIV. Polysulfide Polymes: II. Applications, Polyethers, Part III, Thiokol Chemical Corp., Trenton, New Jersey, p. 115-215.

* cited by examiner

Primary Examiner — Shane Fang
(74) Attorney, Agent, or Firm — Sandra B. Weiss

(57) ABSTRACT

Pre-polymer according to structure (I) $X-(R^2-O)_n-CH_2-O-(R^1-O)_m-CH_2-(O-R^2)_p-X$ (I) wherein $R^1$ and $R^2$ can be the same or different and are selected from alkane chains containing 2-10 carbon atoms, X is a halogen atom, and n, m, and p are integers that can be the same of different and have a value in the range 1-6. The use of this pre-polymer in the preparation of a liquid polysulfide polymer allows better control over the sulfur and oxygen content and the polarity of the resulting polymer.

10 Claims, No Drawings

PROCESS FOR THE PREPARATION OF A POLYSULFIDE

This application is a national stage filing under 35 U.S.C. §371 of PCT/EP2014/062306, filed Jun. 13, 2014, which claims priority to European Patent Application No. 13172268.8, filed Jun. 17, 2013, the contents of which are each incorporated herein by reference in their entireties.

The present invention relates to a process for the preparation of a polysulfide.

Polysulfides are a class of polymers with alternating chains of several sulfur atoms and hydrocarbons. The general formula for the repeating unit is —[R—$S_x$]$_n$—, wherein x indicates the number of sulfur atoms, n indicates the number of repeating units, and R indicates the organic backbone of the polymer. Cured polysulfide polymers are resistant to ageing and weathering, highly elastic from −40 to +120° C., and they offer an outstanding chemical resistance, especially against oil and fuel. Because of their properties, these materials find use as base polymer for sealants applied to fill the joints in pavement, insulation glass units, and aircraft structures.

Polysulfides are conventionally synthesized by condensation polymerization reactions between organic dihalides and alkali metal salts of polysulfide anions. Conventional types of polysulfides include solid and liquid polymers.

Solid polymers have a molecular weight of about $10^5$ g/mol and are prepared from dihaloalkanes (such as 1,2-dichloroethane), alone or in admixture with a bis(2-chloroalkyl)formal, for example bis(2-chloroethyl)formal, and optionally a branching agent such as 1,2,3-trichloropropane.

The disadvantages of the solid polymers based on 1,2-dichloroethane as only dihalide—such as poor flexibility at low temperatures and poor compression properties—have been improved by blending the 1,2-dichloroethane with the bis(2-chloroalkyl)formal and the branching agent.

Liquid polysulfides have a molecular weight of about $10^2$ to $10^3$ g/mol and are generally prepared from a bis(2-chloroalkyl)formal and optionally small amounts of a branching agent like 1,2,3-trichloropropane. The resulting latex is then split into chains of the required lengths by reduction of the disulfide linkages.

A disadvantage of this process is that it does not allow much control over the polarity of the resulting polysulfide.

The polarity of the polysulfide affects its compatibility with surfaces. Polysulfides are often used as sealants for double glazing and in aircrafts. Hence, good compatibility with relatively polar surfaces like glass and metals such as aluminium or steel is required for these applications. The polarity is improved with the introduction of more oxygen relative to sulfur atoms. In addition, the flexibility and elasticity of the polymer at low temperatures and the compatibility of the polymer with plasticizers is improved with higher oxygen contents. On the other hand, the chemical resistance against oil and jet fuel improves with a higher content of sulfur relative to oxygen atoms. For aircraft applications, for instance, this leads to conflicting requirements for the sulfur/oxygen ratio of the polymer.

It would therefore be desirable to provide a process that would allow control over the oxygen and sulfur content of the resulting polymer and the possibility to easily adapt this ratio depending on the particular requirements of the product.

Preparing liquid polymers by splitting the chains of solid polymers derived from either dichloroalkane or a combination of dichloroalkane and bis(2-chloroalkyl)formal would not solve this problem because it would lead to liquid polysulfides having a relatively high sulfur content, a relatively low oxygen content and, thus, a relatively low polarity, without suitable means to adapt these properties.

It is therefore an object of the present invention to provide a liquid polysulfide polymer with improved chemical resistance and compatibility with plasticizers and polar surfaces. It is a further object to provide a process that would allow control over the oxygen and sulfur content of the resulting polymer and the possibility to easily adapt this ratio depending on the particular requirements of the product.

These problems have now been solved by the process according to the present invention, which requires the use of a so-called pre-polymer prepared from (para)formaldehyde, a polyol, and a halo-alcohol.

The present invention therefore relates to a pre-polymer according to structure (I)

$$X—(R^2—O)_n—CH_2—O—(R^1—O)_m—CH_2—(O—R^2)_p—X \quad (I)$$

wherein $R^1$ and $R^2$ can be the same or different and are selected from alkane chains containing 2-10 carbon atoms, preferably 2-6, and most preferably 2-4 carbon atoms, X is a halogen atom selected from Cl, Br, and I, preferably Cl, n, m, and p are integers that can be the same of different and have a value in the range 1-6, preferably 1-4.

Preferably, $R^1$ is —$CH_2$—$CH_2$—.

The preferred nature of $R^2$ is —$CH_2$—$CH_2$—, —$CH_2$—$CH_2$—$CH_2$—, or —$CH_2$—$CH_2$—$CH_2$—$CH_2$—.

The invention also relates to the preparation of this pre-polymer by reacting a polyol with (para)formaldehyde and a halo-alcohol.

The invention further relates to a process for the preparation of a polysulfide comprising the step of reacting a mixture of bis(2-dichloroalkyl)formal and a dihaloalkane with sodium polysulfide in the presence of the pre-polymer.

In this specification, the term "(para)formaldehyde" includes formaldehyde (i.e. $CH_2O$) and the condensation products of formaldehyde having the formula $(CH_2O)_n$ that are conventionally referred to as paraformaldehyde. The value of n in this formula is generally in the range 8-100. In the present invention, the use of paraformaldehyde is preferred over formaldehyde.

The pre-polymer according to structure (I) is obtainable by reacting a polyol with (para)formaldehyde and a halo-alcohol in the presence of an acid catalyst.

Suitable polyols include monoethylene glycol, diethylene glycol, triethylene glycol, tetraethylene glycol, monopropylene glycol, dipropylene glycol, tripropylene glycol, 1,4-butanediol, and mixtures thereof.

Suitable halo-alcohols include chloroalcohols, bromoalcohols, and iodoalcohols, whereby chloroalcohols are preferred. Examples of suitable chloroalcohols are ethylene chlorohydrin (ECH), propylene chlorohydrins, butylene chlorohydrins, pentylene chlorohydrins, and hexylene chlorohydrins. ECH is the most preferred chloroalcohol.

Suitable acid catalysts are HBr, HCl, $H_2SO_4$, $H_3PO_4$, p-toluene sulfonic acid, sulfonic acid, ferric chloride, and cation exchange resins, such as Amberlyst® 15, 31, 35, 36, 39, 119, 131, Lewatite® K1131, K2431, K 2621, and Nafion® SAC-13.

In the formation of the pre-polymer, the molar ratio of (para)formaldehyde (calculated as $CH_2O$) to OH-functionalities of the polyol is preferably in the range 0.8:1-1.5:1, more preferably 0.9:1-1.3:1, and even most preferably 0.9:1-1.2:1.

The molar ratio of halo-alcohol to OH-functionalities of the polyol is preferably in the range 0.9:1-1.5:1, more preferably 0.9:1-1.4:1 and most preferably 1:1-1.2:1.

The molar ratio of (para)formaldehyde (calculated as $CH_2O$) to halo-alcohol is preferably in the range 0.8:1-1.5:1, more preferably 0.9:1-1.3:1, and most preferably 0.9:1-1.2:1.

The amount of acid catalyst is preferably in the range of from 0.1 to 10 wt %, based on the weight of entire reaction mixture.

The reaction towards the pre-polymer is preferably performed by heating the reaction mixture to a temperature in the range 45-80° C., more preferably 50-75° C., and most preferably 55-65° C. This heating is preferably conducted for 10 minutes to 2 hours, more preferably 20 minutes to 1.5 hours and most preferably 30-60 minutes.

This heating step is preferably followed by two azeotropic distillation steps in order to remove reaction water and any excess of halo-alcohol, thereby shifting the equilibrium towards the pre-polymer.

The invention also relates to a process for preparing a polysulfide using the pre-polymer. According to this process, bis(2-dihaloalkyl)formal and a dihaloalkane are reacted with sodium polysulfide in the presence of the pre-polymer.

Suitable bis(2-dihaloalkyl)formals for use in the process of the present invention are bis(2-dichloroalkyl)formals, bis(2-dibromoalkyl)formals, and bis(2-diiodoalkyl)formals. The most preferred bis(2-dihaloalkyl)formal is bis(2-dichloroethyl)formal: $Cl$—$C_2H_4$—$O$—$CH_2$—$O$—$C_2H_4$—$Cl$.

The dihaloalkane to be used in the process of the present invention has the formula X—R—Y, wherein X and Y are both halogen atoms that may be the same or different, and R is an alkane chain with preferably 2-10, more preferably 2-6 carbon atoms. Preferably, the dihaloalkane is an alpha-omega dihaloalkane, meaning that the halogen atoms are located at the opposite ends on the alkane chain. The preferred halogen atom is chlorine. Hence, the dihaloalkane is preferably a dichloroalkane, more preferably an alpha-omega dichloroalkane.

Examples of suitable dichloroalkanes are 1,2-dichloroethane, 1,2-dichloropropane, 1,3-dichloropropane, 1,4-dichlorobutane, 1,5-dichloropentane, 1,6-dichlorohexane, and isomers thereof.

Sodium polysulfide has the formula $Na_2S_x$, wherein x is in the range 2-5, preferably in the range 2-3, and most preferably in the range 2.2-2.5.

The molar ratio bis(2-dihaloalkyl)formal to dihaloalkane to be used in the process according to the present invention is preferably in the range 95:5 to 5:95, more preferably in the range 90:10 to 20:80, and most preferably in the range 80:20 to 50:50.

The molar ratio of sodium polysulfide (calculated as $Na_2S_x$), relative to bis(2-dihaloalkyl)formal, is preferably in the range 0.8-1.4, more preferably 0.9-1.3, and most preferably 1.0-1.2.

The weight ratio bis(2-dihaloalkyl)formal to pre-polymer to be used in the process according to the present invention is preferably in the range 90:10 to 10:90, more preferably in the range 70:30 to 30:70, even more preferably in the range 40:60 to 60:40, and most preferably in the range 45:55 to 55:45.

This process is preferably performed by first preparing a mixture comprising the bis(2-dihaloalkyl)formal, the dihaloalkane, the pre-polymer, and optionally a branching agent, and adding this mixture to an aqueous solution of sodium polysulfide and alkali metal hydroxide. Optionally, a dispersing agent, such as magnesium hydroxide, and/or a wetting agent (e.g. sodium butylnaphthalenesulfonate) may be present in the solution.

The mixture is preferably added slowly, e.g. dropwise, to the solution. The temperature of the solution is preferably in the range 60 to 100° C., more preferably from 80 to 95° C. and most preferably from 85 to 90° C.

The optional branching agent preferably is a trihalide, more preferably 1,2,3-trichloropropane. This branching agent is preferably present in the mixture in an amount of 0.5 to 2 wt %, relative to the weight of bis(2-dihaloalkyl)formal.

After this first step, the resulting reaction mixture is preferably treated with a desulfurization agent (e.g. sodium hydroxide and sodium hydrogen sulfide) to eliminate any labile sulfur atoms. This desulfurization step can be conducted at a preferred temperature of 80-110° C., more preferably 85-105° C., and most preferably 90-100° C. The reaction time is preferably 1-4 hours, more preferably 1-3 hours, and most preferably 1-2 hours.

The obtained high-molecular latex is then preferably subjected to several washing steps in order to remove any soluble salts formed as side products.

In order to obtain a liquid polysulfide, the macromolecules in said latex need to be reduced to the required chain length by reductive splitting of the disulfide bonds. The most common reduction agents are sodium dithionite ($Na_2S_2O_4$) and a combination of NaSH and $Na_2SO_3$. The amount of reduction agent to be used depends on the desired molecular weight, as commonly know in the art.

The preferred reduction agent in the process according to the invention is sodium dithionite. Reductive splitting using sodium dithionite is preferably performed for 20-40 minutes. The temperature preferably ranges from 80 to 110° C., more preferably from 85 to 105° C. and most preferably from 90 to 100° C.

If desired, the splitted disulfide bonds can then be converted into reactive terminal thiol groups by acidification at pH 4-5. Acetic acid is preferably used as acidifier. After this last step, the polysulfide can be washed and dewatered under reduced pressure.

The liquid polysulfide resulting from the process of the present invention has various applications, including the use as binder in sealants, adhesives, and coating compositions, in isocyanate cure, in epoxy-resin cure, and in acrylate resin cure.

EXAMPLES

Example 1—Synthesis of the Pre-Polymer

A mixture of 4 moles paraformaldehyde, 7.5 moles ethylenchlorohydrin (ECH), 1 mole tetraethylene glycol (TEG) and 5.4 g HCl (added as 37% solution; calculated as pure HCl) per mole formaldehyde (calculated as $CH_2O$) was heated with stirring to about 60° C. until the formaldehyde dissolved. The reaction mixture was then subjected to two azeotropic distillation steps under reduced pressure (head temperatures 120 mbar/54° C. and 20 mbar/94° C., respectively) in order to remove reaction water and excess ECH. The resulting product was a pre-polymer according to the present invention.

Comparative Example A—Synthesis of a Polysulfide Polymer without Pre-Polymer

A mixture of 2 moles paraformaldehyde (calculated as $CH_2O$), 5 moles ethylenchlorohydrin (ECH) and 2.7 g HCl (added as 37% solution; calculated as pure HCl) per mole formaldehyde (calculated as $CH_2O$) was heated with stirring to about 60° C. until the formaldehyde dissolved. The resulting reaction mixture was subjected to an azeotropic distillation under reduced pressure as described in Example 1 in order to remove reaction water and excess ECH. The resulting product was bis-(2-chloroethyl)formal (DF).

2.2 moles $Na_2S_x$ (x=2.4), in an aqueous 2.1 mol/l solution, was treated with 25.1 g $MgCl_2$, 12 g 50% NaOH solution (to form in situ $Mg(OH)_2$), and 10 mL of sodium butylnaphthalenesulfonate (a wetting agent) and heated to 88° C. A mixture of 1.32 moles DF, 0.88 moles dichloropropane (DCP) and 2 mole % (based on DF+DCP) of trichloropropane was added dropwise over 1 hour while keeping the temperature between 88° C. and 92° C. After addition of this mixture, the desulfurization agents (0.5 moles NaOH and 0.5 moles NaSH) were added and the reaction mixture was stirred for 2 hours at 100° C. After this time, the formed condensation latex was washed with water several times by decantation in order to remove any soluble salts.

In a further step, the washed latex was treated with 0.18 moles (34 g 90%) sodium dithionite, 0.6 moles NaOH (48.9 g 50%) and 0.2 moles sodium bisulfite (50 mL 39.4% sol.) at 98° C. The reaction mixture was stirred for 30 minutes at this temperature. After that, the product was washed free of soluble salts and was coagulated by acidification with acetic acid to a pH in the range 4-5. After coagulation, the polymer was washed free of acetate ions and dewatered under reduced pressure (90° C., 20 mbar) resulting in a polymer with a number average molecular weight of 1800-2700 g/mol.

This molecular weight was determined by Gel Permeation Chromatography (GPC) using polystyrene standards and by determination of the number of —SH groups by way or titration with iodine, followed by back titration.

Example 2—Synthesis of a Polysulfide Polymer With Pre-Polymer and DF

Comparative Example A was repeated, except that 0.87 moles DF and 0.45 moles of the pre-polymer of Example 1 were used instead of the 1.32 moles of DF used in Comparative Example A.

The resulting polymer had a molecular weight of 2000-3000 g/mol.

The compatibility of the polysulfides according to Comparative Example A and Example 2 with different plasticizers was assessed by visual inspection of cured sealant matrices comprising the polysulfide and the plasticizer. If no migration of plasticizer out of the matrix was observed, the polysulfide and the plasticizer were considered compatible. If migration was observed, they were considered incompatible.

In addition, the adhesion/cohesion behavior of the sealants to a glass substrate was evaluated in accordance with DIN 53504. Adhesion means: no chemical adhesion; only physical adhesion. Cohesion means: chemical adhesion.

TABLE 1

Compatibility to plasticizer

| Plasticizer: | Comp. Ex. A | Ex. 2 |
|---|---|---|
| 3,3'-oxydi-1-propanol dibenzoate | | |
| Compatibitity to sealant formulation | Compatible | Compatible |
| Adhesion behaviour to glass substrate | Cohesive | Cohesive |

TABLE 1-continued

Compatibility to plasticizer

| Plasticizer: | Comp. Ex. A | Ex. 2 |
|---|---|---|
| Alkyl (C7-C9) Benzyl Phthalate | | |
| Compatibitity to sealant formulation | Compatible | Compatible |
| Adhesion behaviour to glass substrate | Cohesive | Cohesive |
| Alkyl (C4) Benzyl Phthalate | | |
| Compatibitity to sealant formulation | Compatible | Compatible |
| Adhesion behaviour to glass substrate | Cohesive | Cohesive |
| Di-alkyl (C9) Phthalate | | |
| Compatibitity to sealant formulation | Incompatible | Compatible |
| Adhesion behaviour to glass substrate | Adhesive | Cohesive |
| Chlorinated paraffins (chlorine content 45-55 wt %) | | |
| Compatibitity to sealant formulation | Compatible | Compatible |
| Adhesion behaviour to glass substrate | Cohesive | Cohesive |

The adhesion behavior of the polysulfides according to Comparative Example A and Example 2 to polymeric and inorganic surfaces was assessed in accordance with DIN 53504. The results are listed in Table 2.

TABLE 2

Adhesion to different surfaces

| Substrate: | Comp. Ex. A | Ex. 2 |
|---|---|---|
| OH-terminiated Polybutadiene-based polyurethanes | | |
| Modulus at 25% elonagtion [N/mm$^2$] | 0.51 | 0.59 |
| Tensile strength [N/mm$^2$] | 1.36 | 1.52 |
| Break-Type (Cohesive/Adhesive) | Adhesive/Cohesive | Cohesive |
| Polyurethanes (PUR) (Polyether-based) | | |
| Modulus at 25% elonagtion [N/mm$^2$] | 0.45 | 0.59 |
| Tensile strength [N/mm$^2$] | 1.53 | 1.62 |
| Break-Type (Cohesive/Adhesive) | Adhesive/Cohesive | Cohesive |
| Polyacrylates (PMMA) | | |
| Modulus at 25% elonagtion [N/mm$^2$] | 0.79 | 0.92 |
| Tensile strength [N/mm$^2$] | 1.57 | 1.69 |
| Break-Type (Cohesive/Adhesive) | Cohesive | Cohesive |
| Polyester (PES) | | |
| Modulus at 25% elonagtion [N/mm$^2$] | 0.72 | 0.84 |
| Tensile strength [N/mm$^2$] | 1.54 | 1.74 |
| Break-Type (Cohesive/Adhesive) | Cohesive | Cohesive |
| Polysulfides (Bis (2-chloroethyl) formal based) | | |
| Modulus at 25% elonagtion [N/mm$^2$] | 1.19 | 1.29 |
| Tensile strength [N/mm$^2$] | 2.25 | 2.38 |
| Break-Type (Cohesive/Adhesive) | Cohesive | Cohesive |
| Epoxies (EP) | | |
| Modulus at 25% elonagtion [N/mm$^2$] | 0.84 | 0.90 |
| Tensile strength [N/mm$^2$] | 1.75 | 1.83 |
| Break-Type (Cohesive/Adhesive) | Cohesive | Cohesive |
| Stainless steel | | |
| Modulus at 25% elonagtion [N/mm$^2$] | 1.05 | 1.09 |
| Tensile strength [N/mm$^2$] | 1.79 | 1.87 |
| Break-Type (Cohesive/Adhesive) | Cohesive | Cohesive |
| Galvanized steel | | |
| Modulus at 25% elonagtion [N/mm$^2$] | 0.99 | 1.14 |
| Tensile strength [N/mm$^2$] | 1.73 | 1.94 |
| Break-Type (Cohesive/Adhesive) | Cohesive | Cohesive |

TABLE 2-continued

Adhesion to different surfaces

| Substrate: | Comp. Ex. A | Ex. 2 |
|---|---|---|
| Aluminium (anodized) | | |
| Modulus at 25% elonagtion [N/mm$^2$] | 0.97 | 1.06 |
| Tensile strength [N/mm$^2$] | 1.67 | 1.88 |
| Break-Type (Cohesive/Adhesive) | Cohesive | Cohesive |
| Glass | | |
| Modulus at 25% elonagtion [N/mm$^2$] | 0.93 | 1.11 |
| Tensile strength [N/mm$^2$] | 1.94 | 1.96 |
| Break-Type (Cohesive/Adhesive) | Cohesive | Cohesive |

The chemical resistance of the two polysulfides towards different liquids was tested by measuring the swelling characteristics in accordance with DIN 53521. The results are listed in Table 3.

TABLE 3

Swelling characteristics

| Liquid: | Comp. Ex. A | Ex. 2 |
|---|---|---|
| Diesel | | |
| after 7 days, 23° C. [%] | 4.73 | 3.99 |
| after 21 days, 23° C. [%] | 7.85 | 6.89 |
| Kerosine | | |
| after 7 days, 23° C. [%] | 4.53 | 3.79 |
| after 21 days, 23° C. [%] | 7.65 | 6.45 |
| Petrol | | |
| after 7 days, 23° C. [%] | 4.41 | 3.75 |
| after 21 days, 23° C. [%] | 7.54 | 6.17 |
| Toluene | | |
| after 7 days, 23° C. [%] | 4.01 | 3.65 |
| after 21 days, 23° C. [%] | 7.24 | 6.03 |
| Ethanol | | |
| after 7 days, 23° C. [%] | 3.37 | 3.09 |
| after 21 days, 23° C. [%] | 5.92 | 5.70 |
| Water | | |
| after 7 days, 23° C. [%] | 2.35 | 2.15 |
| after 21 days, 23° C. [%] | 4.92 | 4.73 |

The above results show that the polysulfide prepared in accordance with the process of the present invention adheres better to a wide range of surfaces, is compatible with a wider range of plasticizers, and has a higher chemical resistance.

The invention claimed is:

1. Process for the preparation of a polysulfide comprising the step of reacting a bis(2-dihaloalkyl)formal and a dihaloalkane with sodium polysulfide in the presence of the pre-polymer according to structure (I)

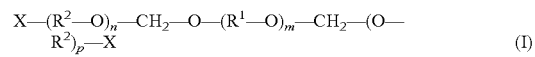

wherein $R^1$ and $R^2$ can be the same or different and are selected from alkane chains containing 2-10 carbon atoms, X is a halogen atom, and n, m, and p are integers that can be the same or different and have a value in the range 1-6.

2. Process according to claim 1 wherein the bis(2-dihaloalkyl)formal is bis(2-dichloroalkyl)formal.

3. Process according to claim 1 wherein the dihaloalkane is an alpha-omega dihaloalkane.

4. Process according to claim 1 wherein the dihaloalkane is a dichloroalkane.

5. Process according to claim 1 wherein the dichloroalkane is selected from the group consisting of 1,2-dichloroethane, 1,2-dichloropropane, 1,3-dichloropropoane, 1,4-dichlorobutane, 1,5-dichloro pentane, 1,6-dichloro hexane, and isomers and combinations thereof.

6. Process according to claim 1 wherein the product resulting from the reaction of the bis(2-dihaloalkyl)formal, the dihaloalkane, and sodium polysulfide in the presence of the pre-polymer is treated with a reducing agent in order to obtain a liquid polysulfide.

7. Process for the preparation of a polysulfide comprising the step of reacting a bis(2-dihaloalkyl)formal and a dihaloalkane with sodium polysulfide in the presence of a pre-polymer obtained by a process wherein a polyol is reacted with (para)formaldehyde and a halo-alcohol in the presence of an acid catalyst.

8. Process according to claim 7 wherein the polyol is selected from the group consisting of monoethylene glycol, diethylene glycol, triethylene glycol, tetraethylene glycol, monopropyele glycol, dipropylene glycol, tripropylene glycol, 1,4-butanediol, and mixtures thereof.

9. Process according to claim 7 wherein the halo-alcohol is a chloro-alcohol.

10. Process according to claim 9 wherein the chloro-alcohol is ethylene chlorohydrin.

* * * * *